United States Patent [19]

Kirsch

[11] Patent Number: Plant 6,167

[45] Date of Patent: May 3, 1988

[54] LILY PLANT NAMED STARSHELL

[75] Inventor: Ted T. Kirsch, Myrtle Point, Oreg.

[73] Assignee: Melridge Inc., Gresham, Oreg.

[21] Appl. No.: 860,861

[22] Filed: May 8, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; W. Dennis Drehkoff

[57] ABSTRACT

A new and distinct lily cultivar of the Oriental hybrid type characterized by its very large, somewhat upward facing, oval shaped flowers with an unusual and distinctive color pattern, the midrib of each flower tepal being colored a rich red-purple color which suffuses outwardly through a light pink to a pure white margin, each tepal being copiously marked on each side of the midrib with maculae of red-purple color over the middle 12 cm. of each tepal.

1 Drawing Sheet

BACKGROUND OF THE INVENTION

This new variety of lily plant originated as a seedling of unknown parentage discovered by me at my nursery in Arcata, Calif. Its large and richly colored flowers, in combination with its vigorous growth habit, prompted me to propagate this seedling for further evaluation. Initial propagation was done by me by bulb scale propagation, which proved to be sufficiently successful to warrant continuous propagation through successive generations under my direction at Arcata, Calif., by bulb scale propagation, natural propagation from bulblets and division, and tissue culture propagation from bulblets and division, and tissue culture propagation originating from bulb scales. The successive generations have demonstrated that the novel and distinctive characteristics of my new variety of lily are fixed and hold true under asexual propagation from generation to generation.

During the course of my evaluation of this new seedling, it has demonstrated that the distinctive characteristics of this plant make it a valuable addition to the commercial propagation of this variety for the production of cut flower lilies. Also, I found that this plant retains its large flower size and good bud color when forced into flower out-of-season from bulbs which have been dug at the proper stage of maturity and properly precooled, the performance being very reliable even during periods of relatively low light.

DESCRIPTION OF THE DRAWING

This new variety of Oriental lily is illustrated in the accompanying photographic drawing which, in the upper view, shows a face view of a typical flower and the lower view shows a silhouette of a group of the flowers, both views illustrating the large, richly colored, bowl-shaped flower form, the color rendition being as nearly true as can be reasonably obtained by conventional photographic procedures.

DESCRIPTION OF THE NEW PLANT

The following is a detailed description of my new variety of Oriental hybrid lily, with nomenclature according to The International Lily Register (The Royal Horticultural Society, London, 1969) and with color designations according to The R.H.S. Colour Chart published in 1966. These observations were made on field grown plants at Arcata, Calif., in the summer of 1985.

THE PLANT

Origin: Seedling.

Parentage: Unknown.

Classification:

*Botanic.*—Hybrid Lilium Cultivar; Division VII-B of The Horticultural Classification of Lilies by The Royal Horticultural Society.

*Commercial.*—Oriental Hybrid Lily.

Form: Single stem, erect and bushy.

Height: About 65 to 100 cm.

Growth: Vigorous, compact, sturdy and with good strength.

Foliage:

*Quantity.*—Abundant.

*Leaf size.*—Ranging from about 10 cm. long and 2 cm. wide at the top of the stem to about 5 cm. long and 2 cm. wide at the bottom.

*Leaf shape.*—Broad lanceolate.

*Texture.*—Leathery.

*Aspect.*—Glossy.

*Color.*—Medium green.

Bulbs:

*Size.*—Varying up to 30 cm. in circumference depending upon age.

*Color.*—White, with flushes of soft pink or yellow which deepen as the bulbs become larger or are exposed to light.

THE BUD

Form: Generally ovate, urn-shaped with obtuse apex.

Size: Average, about 10 to 12 cm. long and 10 cm. in circumference, depending upon light and nutritional levels.

Opening rate: The bud opens slowly in response to morning light; the buds open successively from the lowermost to the uppermost as is typical of Lilium.

Color: Palest pink with old rose tips of red-purple, 59C-D, just before the buds open shading to a softer tone at the tips of the bud and between the ribs.

Peduncle:

*Length.*—About 2 to 3 cm. The peduncle may elongate under low light conditions or when bulbs have been improperly stored prior to forcing.

*Color.*—Dark green.

THE FLOWER

Blooming habit: This plant flowers once and profusely in midseason, generally flowering in late July under field conditions in Arcata, Calif. When properly forced from appropriately precooled bulbs, this plant flowers in 95 to 110 days in greenhouse.

Size: Large; averaging about 20 to 22 cm. in diameter with the tepals recurving to form a bowl about 15 to 16 cm. wide and about 4 to 4.5 cm. deep.

Borne: As a compact raceme with each pedicel bearing one bud, with the bulbs of typical commercial size bearing an average of about 5 to 8 flowers.

Shape: Bowl-shaped with broad and generally overlapping tepals which are slightly recurved.

Tepalage:

*Number.*—Six.

*Form.*—The tepals are generally ovate with the inner tepals averaging about 5 cm. wide and the outer tepals about 3 cm. wide. The inner tepals overlap slightly.

*Color.*—Each tepal has a band of Red-Purple color, RHS 58A-B (occasionally 57B), along the tepal midrib which shades gradually into a light Rose Bengal, 57D, approaching the tepal margins. The inner tepals have a white margin about 5 to 6 mm. wide and the outer tepals have a white margin about 2 to 4 mm. wide and the tepal margins may be lightly frilled. The nectaries are green with a yellow margin about 2 to 4 mm. wide and the very conspicuous papillae are of a 58A-B coloration.

*Tepal longevity.*—The tepals stay on the stem about two to three weeks.

*Color change.*—The color fades slightly and becomes more brown as the flower ages, or in intense light and heat. Under cool conditions, the color is richer and is retained longer.

Pedicel:

*Length.*—About 7 to 8 cm.

*Color.*—Dark green.

*Character.*—Ascending at an angle of about 45° from the stem.

Disease resistance: The flower and plant are adequately resistant to disease as observed in northwestern California and in western Oregon.

Fragrance: The fragrance is heavy and sweet.

Lasting quality: The flower is long lasting, both on field grown plants and on forced potted cultivars.

REPRODUCTIVE ORGANS

Stamens:

*Number.*—Six.

*Arrangement.*—Typical of Lilium.

*Color.*—169A-B (may be 163A if "bleached" in full sun).

Filaments:

*Length.*—About 7 to 8 cm.

*Color.*—Light green.

Pistil:

*Number.*—One per flower.

Style:

*Color.*—Light green.

Stigma:

*Size.*—About 5 mm. wide.

*Color.*—Medium to light purple-grey.

Ovary: Typical of Lilium.

I claim:

1. A new and distinct variety of Oriental hybrid lily, substantially as herein shown and described, characterized by its slightly upright and outward facing bowl-shaped flowers of large size, good substance and form, and borne as a raceme with ascending pedicels on a strong stem of medium height.

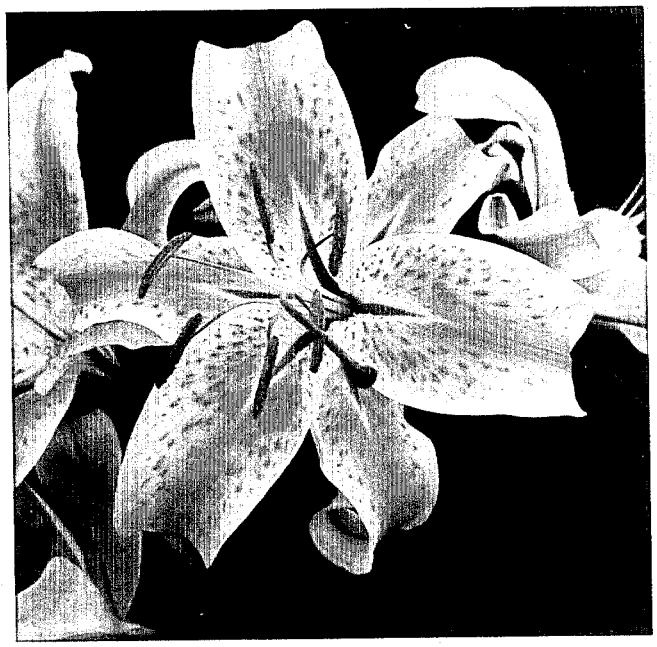
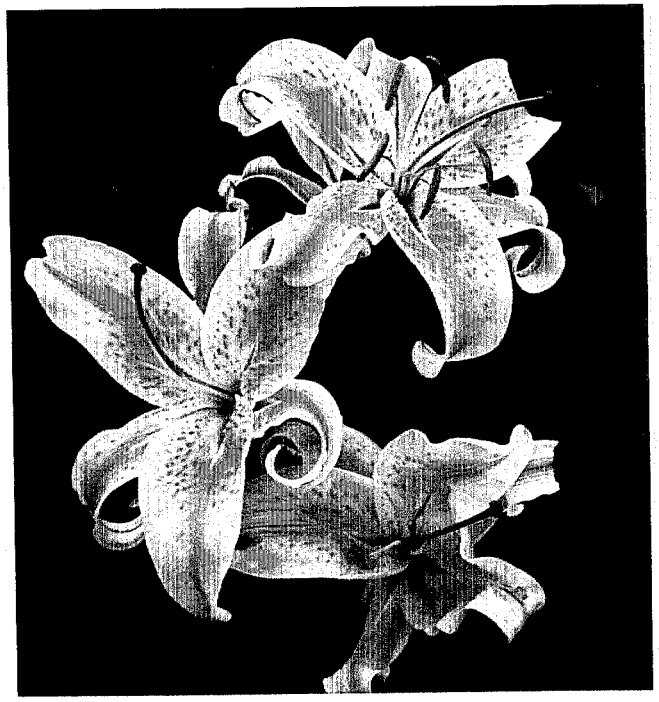

* * * * *